DISTINCT VARIETY OF PHILODENDRON PLANT
Filed April 10, 1972
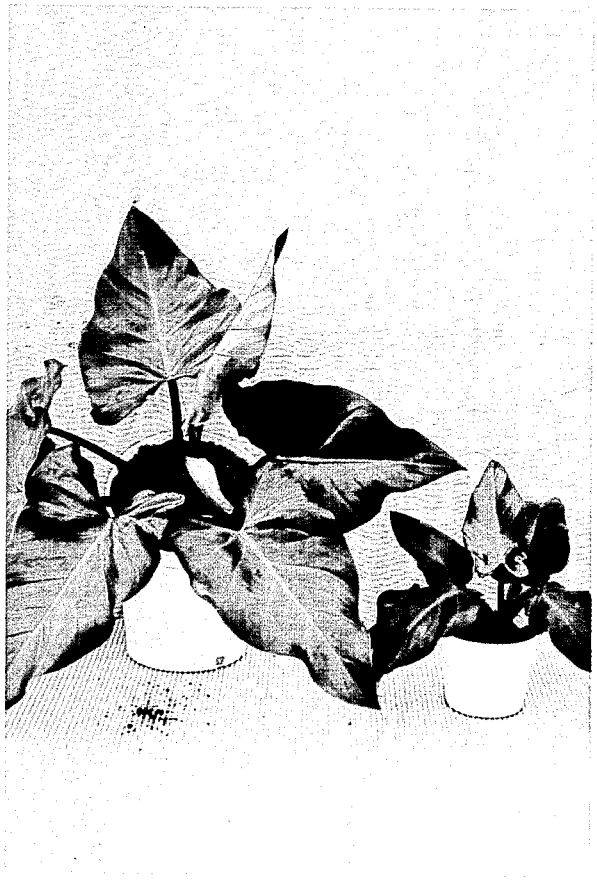

United States Patent Office

Plant Pat. 3,398
Patented Sept. 18, 1973

3,398

DISTINCT VARIETY OF PHILODENDRON PLANT

Robert H. McColley, P.O. Box 17126,
Orlando, Fla. 32810

Filed Apr. 10, 1972, Ser. No. 242,848
Int. Cl. A01h 5/00
U.S. Cl. Plt.—88 1 Claim

ABSTRACT OF THE DISCLOSURE

There is disclosed a new variety of Philodendron plant, characterized by the substantial volume of moderate reddish brown leaves at maturity, compact dense growth, the leaves being very thick and rubbery with large diameter stems, the general color of the plant being distinctive in that it includes the reddish and green contrast resulting from the breeding.

DESCRIPTION OF THE INVENTION

My present invention comprises a new and distinct variety of Philodendron plant, result of selfing an unpatented inbred seedling (not named) whose parentage involves *Philodendrons imbe, hastatum, erubescens, wendlandii* and an unnamed unpatented species.

The new variety is unlike any Philodendron in cultivation generally, nor like any of those described by Bailey, Graf or Das Pflanzenreich.

Thus it is rather difficult to compare the plant with any known plant but it is contrasted in any event with another invention of mine, the Philodendron disclosed in Pat. No. P.P. 3,034.

To assist in recognition of the plant of my new variety, I have hereinafter set forth a number of characteristics by which the same may be recognized and identified, these characteristics coming through in repeated asexual reproduction including but not limited to the following:

(1) Ovate leaf
(2) Cordate leaf base
(3) Acuminate leaf tip
(4) Distinctive leaf margin
(5) Pinnate leaf veination
(6) Alternate leaf placement
(7) Undulate leaf surface
(8) Raised mid-rib, sunken veins
(9) Dark red petioles, almost blood-like, ½ to ¾ the length of the leaf itself.
  (a) These petioles are winged in the juvenile stage.
  (b) At the mature stage, petioles are round and very sturdy.
(10) Internodes vary ⅜" to 1", depending on the growth factors
(11) Dark, blood-red stem
(12) Dark green leaves with bright red margins.
  (a) New or immature leaves are red, turning to dark green as they mature.
(13) Horizontal to elevated leaf placement
(14) Semi-erect petioles The foregoing visual characteristics are supplemented by other growth characteristics and the superior nature of the same is emphasized by the fact that the plant withstands extreme low light intensity and a low moisture content of the soil for weeks without visible damage.

Even high temperatures, as high as 100 degrees F., are able to be withstood by the plants of my new variety.

An interesting aspect of the leaves is the fact that they are unusually thick (.016" to .020"), very rubbery to the touch and capable of withstanding bruising and dehydration without wilting.

In many of my current plants, as well as the one of the subject invention, I have developed a substantial resistance to bacterial soft rot and almost an immunity to "shot gun fungus" which is a dehydration problem of Philodendrons commonly observed.

Since the plant grows in a compact manner, it does not require staking, and further it grows relatively slowly when in the home or under other interior conditions, it retains a desired form and size longer than many other known varieties.

My new variety has been asexually reproduced by tip cuttings in the vicinity of Orlando, Fla., and has been found to retain the distinctive characteristics hereinbefore set forth through successive asexual reproduction.

The detailed specifications and descriptions hereinafter set forth are based on observations made in a greenhouse in Orlando, Fla. As will be readily understood, the specifications might vary significantly with varying environmental conditions, but where the conditions are consistent, the plants will likewise run consistently.

The accompanying drawing forming a part hereof, shows a typical plant of my new variety, the color being as nearly true as possible with color illustrations of this type. Color reference are made to Nickerson Color Fan published by Munsell Color Company, the observations being recorded by daylight illumination under vinyl of not more than 30% shade.

(I) Form characteristics:

(1) Leaf shape:
  (a) Mature ..... Ovate.
  (b) Immature ..... Do.
  (c) Tip ..... Acute.
  (d) Base:
    (1) Mature ..... Auriculate.
    (2) Immature ..... Obtuse to auriculate.
  (e) Displacement ..... Undulate.
  (f) Margin ..... Entire.
  (g) Veination ..... Raised midrib, sunken veins.
(2) Leaf attachment ..... Stalked.
(3) Leaf arrangement ..... Alternate; horizontal to elevated.
(4) Petiole ..... Very short—semi-erect.
(5) Stem ..... Very short—internodes ⅜" to 1".
(6) Overall appearance ..... Dense.

(II) Size characteristics of typical commercial size:

(1) Leaf itself:
  (a) Width—widest point 4½ inches to 6½ inches
  (b) Width—1" from tip 1 inch
  (c) Length ..... 6 inches to 9½ inches
  (d) Thickness ..... .016 inch to .020 inch
(2) Petiole length ..... 3 inches to 5 inches
(3) Internode spacing ..... ⅜ inches to 1 inch
(4) Stem diameter ..... ½ to 1 inch (III) Color characteristics:

(1) Leaf (mature):
  (a) Top ..... 5GY 3/2
  (b) Bottom ..... 7.5R 3/6
  (c) Margin ..... 7.5R 3/6
(2) Leaf immature:
  (a) Top ..... 7.5R 4/5
  (b) Bottom ..... 7.5R 3/6
  (c) Margin ..... 7.5R 3/6
(3) Leaf midrib:
  (a) Top ..... 5R 4/12
  (b) Bottom ..... 5R 3/7
(4) Stem and petiole ..... 2.5R 3/7

I claim:

1. A new and distinct variety of Philodendron plant, substantially as herein disclosed, characterized as to novelty by its superior, dense, compact growth and long keeping qualities under arid conditions, requiring little attention while displaying unusual form and a substantial volume of moderate reddish brown leaves at maturity, said leaves being very thick and rubbery on large diameter stems.

No references cited.

ROBERT E. BAGWILL, Primary Examiner